United States Patent [19]

Neuzil

[11] 3,997,619

[45] Dec. 14, 1976

[54] PROCESS FOR THE SEPARATION OF ETHYLBENZENE

[75] Inventor: Richard W. Neuzil, Downers Grove, Ill.

[73] Assignee: Universal Oil Products Company, Des Plaines, Ill.

[22] Filed: May 14, 1975

[21] Appl. No.: 577,489

[52] U.S. Cl. .................... 260/674 SA; 208/310 Z
[51] Int. Cl.$^2$ ........................................ C07C 7/13
[58] Field of Search .......... 260/674 SA; 208/310 Z

[56] References Cited

UNITED STATES PATENTS

| 3,636,121 | 1/1972 | Stine et al. | 260/674 |
|---|---|---|---|
| 3,734,974 | 5/1973 | Neuzil | 260/674 |
| 3,793,386 | 2/1974 | Davis | 260/674 |
| 3,917,734 | 11/1975 | de Rosset | 260/674 |

Primary Examiner—Delbert E. Gantz
Assistant Examiner—C. E. Spresser
Attorney, Agent, or Firm—James R. Hoatson, Jr.; Thomas K. McBride; William H. Page, II

[57] ABSTRACT

An adsorptive separation process for separating ethylbenzene from a feed mixture comprising ethylbenzene and a plurality of xylene isomers, which process comprises contacting the feed mixture with a crystalline aluminosilicate adsorbent comprising a sodium-type Y zeolite having a $SiO_2/Al_2O_3$ mole ratio greater than about 4.5, selectively adsorbing substantially all of the said xylene isomers to the substantial exclusion of the ethylbenzene and recovering high-purity ethylbenzene. A desorption step may then be used to desorb the adsorbed xylene isomers. The process can be either in the liquid or vapor phase.

20 Claims, No Drawings

PROCESS FOR THE SEPARATION OF ETHYLBENZENE

BACKGROUND OF THE INVENTION

1. Field of the Invention

The field of art to which the claimed invention pertains is solid-bed adsorptive separation. More specifically, the claimed invention relates to a process for the separation of ethylbenzene from a feed mixture comprising ethylbenzene and xylene isomers which process employs a solid adsorbent which selectively removes the xylene isomers from the feed mixture thereby producing a fluid raffinate stream comprising ethylbenzene.

2. Description of the Prior Art

It is well known in the separation art that certain crystalline aluminosilicates can be used to separate hydrocarbons species from mixtures thereof. In particular, the separation of normal paraffins from branched chained paraffins can be accomplished by using the type A zeolite which has pore openings from 3 to about 5 Angstroms. Such a separation process is disclosed for example in U.S. Pat. Nos. 2,985,589 and 3,201,491. These adsorbents allow a separation based on the physical size differences in the molecules by allowing the smaller or normal hydrocarbons to be passed into the cavities within the crystalline aluminosilicate adsorbent, while excluding the larger or branched chain molecules.

U.S. Pat. Nos. 3,265,750 and 3,510,423 for example disclose processes in which larger pore diameter zeolites such as the type X or type Y structured zeolites can be used to separate olefinic hydrocarbons.

In addition to separating hydrocarbon types, the type X or type Y zeolites have also been employed in processes to separate individual hydrocarbon isomers. In the process described in U.S. Patent 3,114,782 for example, a particular zeolite is used as a adsorbent to separate alkyl-trisubstituted benzene; and in U.S. Pat. No. 3,668,267 a particular zeolite is used to separate specific alkyl-substituted naphthalenes.

Because of the commercial importance of para-xylene, the more well-known and extensively used hydrocarbon isomer separation processes are those for separating para-xylene. Para-xylene is used in the manufacture of terephthalic acid which in turn is subsequently employed in the manufacture of various synthetic fibers such as Dacron which fiber is a trademarked product of the duPont Company. In processes described in U.S. Pat. Nos. 3,558,730; 3,558,732; 3,626,020; 3,663,638; and 3,734,974 for example adsorbents comprising particular zeolites are used to separate para-xylene from feed mixtures comprising para-xylene and at least one other xylene isomer by selectively adsorbing para-xylene over the other xylene isomers. In such processes the adsorbents used are para-xylene selective; para-xylene is selectively adsorbed and recovered as an extract component while the rest of the xylenes and ethylbenzenes are all relatively unadsorbed with respect to para-xylene and are recovered as raffinate components. In contrast, the present invention relates to a process for the separation of ethylbenzene from a feed mixture comprising ethylbenzene and a plurality of xylene isomers in which essentially all of the xylene isomers are selectively adsorbed and recovered as extract components leaving only ethylbenzene relatively unadsorbed with is recovered in high-purity as a raffinate component. The adsorbent employed is "all-xylene" selective rather than para-xylene selective as are the adsorbents used in para-xylene separation process thus distinguishing my process from the prior art separation processes. Specifically, I have found that adsorbents comprising sodium-type Y zeolites having a $SiO_2/Al_2O_3$ mole ratio greater than about 4.5 exhibit selectivity for all the xylene isomers with respect to ethylbenzene thereby making separation of ethylbenzene from xylene isomers by solid-bed selective adsorption possible.

Ethylbenzene is used as a raw material in the production of styrene monomer. Ethylbenzene can be and is commercially produced from the alkylation of benzene with ethylene. The cost of and competing demands for necessary benzene and ethylbenzene feed streams have, however, prompted new efforts to recover ethylbenzene from various $C_8$ aromatic feed streams which already contain ethylbenzene. Such feed streams for instance, include $C_8$ aromatic extracts produced by a typical solvent extraction process from a pyrolysis gasoline or from a naphtha which has been reformed with a platinum-halogen-containing catalyst. Additionally, $C_8$ aromatic cuts of hydrogenated pyrolysis naphthas or reformates prepared by fractionation without solvent extraction contain varying amounts of ethylbenzene. The particular utility of the process of my invention is that it offers a method for recovering ethylbenzene from a feed stream which already contains ethylbenzene.

Ethylbenzene can, of course, be separated from the xylene isomers by fractionation but because its boiling point is within about 4° F. of that of para-xylene, the fractionation can be achieved only with the more intricate super-fractionators. Typical ethylbenzene fractionators contain 300 to 400 actual trays and require about a 25–50 to 1 reflux to feed ratio. The process of my invention therefore offers a competitive alternative to the separation of ethylbenzene by super-fractionation.

SUMMARY OF THE INVENTION

It is, accordingly, a broad objective of my invention to provide a process for the separation of ethylbenzene from a feed mixture comprising ethylbenzene and a plurality of xylene isomers.

In brief summary, my invention is, in one embodiment, a process for separating ethylbenzene from a feed mixture comprising ethylbenzene and a plurality of xylene isomers which process comprises contacting said mixture with a crystalline aluminosilicate adsorbent comprising sodium-type Y zeolite having a $SiO_2/Al_2O_3$ mole ratio of greater than about 4.5, selectively adsorbing substantially all of said xylene isomers to the substantial exclusion of ethylbenzene, and thereafter recovering high-purity ethylbenzene as a raffinate component.

My invention is, in another embodiment, a process for separating ethylbenzene isomer from a hydrocarbon feed mixture comprising ethylbenzene and a plurality of xylene isomers which process comprises the steps of: contacting said mixture with an adsorbent comprising sodium-type Y zeolites having a $SiO_2/Al_2O_3$ mole ratio of greater than about 4.5 at adsorption conditions to effect the selective adsorption of substantially all of said xylene isomers to the substantial exclusion of ethylbenzene; withdrawing from the adsorbent a raffinate stream comprising less selectively adsorbed ethylbenzene; contacting the adsorbent at desorption conditions with a desorbent material having a boiling point substantially different from that of the feed mixture to effect the removal of the selectively adsorbed xylene isomers; and, withdrawing from the solid adsorbent bed an extract stream comprising said xylene isomers.

Other embodiments and objects of the present invention encompass details about feed mixtures, adsorbents, desorbents, and operating conditions all of which are hereinafter disclosed in the following discussion of each of these facets of the present invention.

DESCRIPTION OF THE INVENTION

Feed mixtures which can be utilized in the process of this invention will comprise ethylbenzene and a plurality of xylene isomers. Mixtures containing substantial quantities of ethylbenzene and the xylene isomers generally are produced by reforming and isomerization processes, processes which are well known to the refining and petrochemical arts. In reforming processes, a naphtha feed is contacted with a platinum-halogen-containing catalyst at severities selected to produce an effluent containing $C_8$ aromatic isomers. Generally the reformate is then fractionated to concentrate the $C_8$ aromatic isomers in a $C_8$ fraction. The $C_8$ aromatic isomers may then be further concentrated by solvent extraction processes. Xylene isomerization processes isomerize at isomerization conditions a xylene mixture which is deficient in one or more isomers to give an effluent containing approximately equilibrium quantities of the $C_8$ aromatic isomers. The equilibrium compositions of the xylene isomers and ethylbenzene at various temperatures are shown in Table 1 below.

Table 1

| Equilibrium $C_8$ Aromatic Compositions* | | | |
|---|---|---|---|
| Temperature, ° C. | 327 | 427 | 527 |
| Mole percent of isomers | | | |
| Ethylbenzene | 6 | 8 | 11 |
| Para-xylene | 22 | 22 | 21 |
| Meta-xylene | 50 | 48 | 45 |
| Ortho-xylene | 22 | 22 | 23 |

*Based on API sources

Feed streams to the process of my invention can contain any two or all three of the xylene isomers in addition to ethylbenzene. Extracted and unextracted $C_8$ reformate fractions and isomerates from xylene isomerization processes containing all of the xylene isomers can be charged as feed streams directly to this process. Feed streams to my process can also comprise effluent streams from processes which have removed varying amounts of one or more xylene isomers. As an example, at least a portion of the ortho-xylene may have been previously removed by fractionation from a feed mixture containing the xylene isomers. Ortho-xylene has a boiling point of about 6° F. higher than that of the nearest other $C_8$ aromatic (meta-xylene) and hence can be removed as a bottoms product from orthoxylene fractionator towers. Such towers will typically contain about 100 to 105 actual trays and will operate with about a 5–8 to 1 reflux to feed ratio. The concentration of ortho-xylene in the effluent from this fractionation process which can be used as a feedstream to my process will then be less than the concentrations of either para-xylene or meta-xylene. Alternatively at least a portion of the para-xylene may have been previously removed from a feed mixture containing the xylene isomers by a fractional crystallization process or by a solid-bed selective adsorptive process or by a combination of both. In this situation, the concentration of para-xylene in the effluent which is now charged as a feed stream to my process will be less than the concentrations of either ortho-xylene or meta-xylene. As another alternative, perhaps at least a portion of both ortho- and para-xylene will have been previously removed, by the processes described above, from a feed mixture containing the xylene isomers. The concentration of both ortho-xylene and para-xylene in this feed stream to my process would then each be less than that of meta-xylene.

Feed mixtures may also contain small quantities of nonaromatics such as straight or branched chain paraffins, cycloparaffins, or olefinic materials. However, since separation of ethylbenzene from a feed mixture by selective adsorption of the xylenes present in the feed mixture on a zeolite adsorbent apparently takes place because of a rather delicate acidity/basicity difference between the xylene isomers and the adsorbent compared to that between ethylbenzene and the adsorbent, it is preferred that these contaminants, especially olefins, be less than about 20 vol. % of the feed mixture passed into the process and more preferably be less than about 10 vol. %, so that this difference is not upset. Another reason for having minimum concentrations of nonaromatics in the feed mixture is that all unadsorbed components will appear in the raffinate stream along with ethylbenzene. Unless these components are later removed from the raffinate stream, the purity of the ethylbenzene will be decreased.

To separate ethylbenzene from a feed mixture containing ethylbenzene and at least one xylene isomer, the mixture is contacted with the adsorbent comprising a crystalline aluminosilicate and the xylene isomers are more selectively adsorbed and retained by the adsorbent while the less selectively adsorbed ethylbenzene is removed from the interstitial void spaces between the particles of adsorbent and the surface of the adsorbent. The adsorbent containing the more selectively adsorbed xylene isomers is referred to as a "rich" adsorbent—rich in the more selectively adsorbed xylene isomers.

A more selectively adsorbed isomer is commonly referred to as an extract component of the feed mixture, while a less selectively adsorbed component is referred to as a raffinate component. Fluid streams leaving the adsorbent comprising an extract component and comprising a raffinate component are referred to, respectively, as the extract stream and the raffinate stream. Since all of the xylene isomers will be selectively adsorbed with respect to ethylbenzene, the extract stream will contain as extract components all of the xylene isomers appearing in the feed mixture and the raffinate stream will contain essentially only ethylbenzene as the raffinate component.

Although it is possible by the process of this invention to produce high purity (98% or greater, expressed as a percent of $C_8$ aromatics present) ethylbenzene at high recoveries, it will be appreciated that an extract component is never completely adsorbed by the adsorbent, nor is a raffinate component completely non-adsorbed by the adsorbent. Therefore, small amounts of a raffinate component can appear in the extract stream and, likewise, small amounts of an extract component can appear in the raffinate stream. The extract and raffinate streams then are further distinguished from each other and from the feed mixture by the ratio of the $C_8$ aromatic isomers appearing in the particular stream. More specifically the ratio of a more selectively adsorbed xylene isomer to the less selectively adsorbed ethylbenzene will be lowest in the raffinate stream, next lowest in the feed mixture, and the highest in the extract stream. Likewise, the ratio of the less selectively adsorbed ethylbenzene to a more selectively adsorbed xylene isomer will be highest in the raffinate stream, next highest in the feed mixture, and the lowest in the extract stream.

The adsorbent can be contained in one or more chambers where through programed flow into and out of the chamber separation of the isomers is effected. The adsorbent will preferably be contacted with a desorbent material which is capable of displacing the adsorbed xylene isomer from the adsorbent. Alternatively, the adsorbed xylene isomer could be removed from the adsorbent by purging or by increasing the temperature of the adsorbent or by decreasing the pressure of the chamber or vessel containing the adsorbent or by a combination of these means.

The adsorbent may be employed in the form of a dense compact fixed bed which is alternatively contacted with the feed mixture and a desorbent material (hereinafter described in more detail). In the simplest embodiment of the invention the adsorbent is employed in the form of a single static bed in which case the process is only semi-continuous. A set of two or more static beds may be employed in fixed-bed contacting with appropriate valving so that the feed mixture is passed through one or more adsorbent beds while the desorbent material is passed through one or more of the other beds in the set. The flow of feed mixture and desorbent material may be either up or down through the desorbent. Any of the conventional apparatus employed in static bed fluid-solid contacting may be used.

Countercurrent moving-bed or simulated countercurrent moving-bed liquid flow systems, however, have a much greater separation efficiency the fixed adsorbent bed systems and are therefore preferred. In the moving-bed or simulated moving-bed processes the adsorption and desorption operations are continuously taking place which allows both continuous production of an extract and a raffinate stream and the continual use of feed and desorbent streams. One preferred processing flow scheme which can be utilized to effect the process of this invention includes what is known in the art as the simulated moving-bed countercurrent system. The operating principles and sequence of such a flow system are described in U.S. Pat. No. 2,985,589 issued to D. B. Broughton which patent is incorporated herein by specific reference thereto. A preferred embodiment of this process will utilize the simulated moving-bed countercurrent system disclosed therein and will comprise the steps of: contacting a feed mixture comprising ethylbenzene and a plurality of xylene isomers at adsorption conditions with a particular zeolitic adsorbent to effect the selective adsorption of the xylene isomers; withdrawing from the adsorbent bed a stream comprising less selectively adsorbed ethylbenzene; contacting the adsorbent at desorption conditions with a desorbent material to effect the removal of the selectively adsorbed xylene isomers from the adsorbent; and, withdrawing from the adsorbent a stream comprising desorbent material and the selectively adsorbed xylene isomers.

Adsorption and desorption conditions for adsorptive separation processes can generally be either in the liquid or vapor phase or both but for aromatic isomer separation processes employing zeolitic adsorbents all liquid-phase operations are usually preferred because of the lower temperature requirements and the slightly improved selectivities associated with the lower temperatures. Preferred adsorption conditions for the process of this invention will include temperatures within the range of from about 100° to about 450° F. and will include pressures in the range from about atmospheric to about 500 psig. Pressures higher than about 500 psig. do not appear to affect the selectivity to a measurable amount and additionally would increase the cost of the process. Desorption conditions for the process of the invention shall generally include the same range of temperatures and pressures as described for adsorption operations. The desorption of the selectively adsorbed isomer could also be effected at subatmosperhic pressures or elevated temperatures or both or by vacuum purging of the adsorbent to remove the adsorbed isomer but this process is not directed to these desorption methods.

The desorbent materials which can be used in the various processing schemes employing this adsorbent will vary depending on the type of operation employed. The term "desorbent material" as used herein shall mean any fluid substance capable of removing a selectively adsorbed feed component from the adsorbent. In the swing-bed system in which the selectively adsorbed feed component is removed from the adsorbent by a purge stream, desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent.

However, in adsorptive separation processes which employ zeolitic adsorbents and which are generally operated at substantially contant pressures and temperatures to insure liquid phase, the desorbent material relied upon must be judiciously selected to satisfy several criteria. First, the desorbent material must displace the adsorbed feed component from the adsorbent with reasonable mass flow rates without itself being so strongly adsorbed as to unduly prevent the extract component from displacing the desorbent material in a following adsorption cycle. Secondly, desorbent materials must be compatable with the particular adsorbent and the particular feed mixture. More specifically, they must not reduce or destroy the critical selectivity of the adsorbent for the extract components with respect to the raffinate component.

Desorbent materials to be used in the process of this invention should additionally be substances which are easily separable from the feed mixture that is passed into the process. After desorbing the extract components of the feed, both desorbent material and the extract components are removed in admixture from the adsorbent. Likewise, the raffinate component ethylbenzene is withdrawn from the adsorbent in admixture with desorbent material. Without a method of separating desorbent material, such as distillation, the purity of neither the extract components nor the raffinate component would not be very high. It is therefore contemplated that any desorbent material used in this process will have a substantially different average boiling point than that of the feed mixture. The use of a desorbent material having a substantially different average boiling point than that of the feed allows separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 15° F. The boiling range of the desorbent material may be higher or lower than that of the feed mixture.

In the preferred isothermal, isobaric, liquid-phase operation of the process of my invention, I have found that desorbent materials comprising mono-aromatic hydrocarbons are particularly effective. Specifically, desorbent materials comprising toluene are especially preferred for this type of operation. Mixtures of toluene with paraffins are also effective as desorbent materials. Such paraffins must be compatable with the adsorbent and feed mixture as described above and must be easily separable from the feed mixture. The paraffins can include straight or branched chain paraffins or cycloparaffins which meet these criteria. Typical concentrations of toluene in such mixtures can be from a few volume percent up to near 100 vol. % of the total desorbent material mixture but such concentrations preferably will be within the range of from about 50 vol. % to about 100 vol. % of the mixture.

With the operation of my process now in mind, one can appreciate that certain characteristics of adsorbents are highly desirable, if not absolutely necessary, to the successful operation of a selective adsorption process. Among such characteristics are: adsorptive capacity for some volume of an extract component per volume of adsorbent; the selective adsorption of extract components with respect to a raffinate component and the desorbent material; and sufficiently fast rates of adsorption and desorption of the extract components to and from the adsorbent.

Capacity of the adsorbent for adsorbing a specific volume of one or more extract component is, of course, a necessity; without such capacity the adsorbent is useless for adsorptive separation. Furthermore, the higher the adsorbent's capacity for extract component the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions.

Relative selectivity is shown as equation 1 below:

Equation 1

$$\text{Selectivity} = (B) = \frac{[\text{vol. percent } C/\text{vol. percent } D]_A}{[\text{vol. percent } C/\text{vol. percent } D]_U}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases.

Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Desorbent materials ideally would have a selectivity equal to about 1 or slightly less than 1 with respect to an extract component.

The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

In order to test various adsorbents and desorbent material with a particular feed mixture to measure the adsorbent characteristics of adsorptive capacity and selectivity and exchange rate a dynamic testing apparatus is employed. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze "on-stream" the effluent stream leaving the adsorbent chamber.

A pulse test, performed using this apparatus and the following general procedure, is used to determine selectivities and other data for various adsorbent systems. The adsorbent is filled to equilibrium with a particular desorbent by passing the desorbent material through the adsorbent chamber. At a convenient time, a pulse of feed containing known concentrations of a non-adsorbed paraffinic tracer (n-nonane for instance)

and of the particular $C_8$ aromatic isomers all diluted in desorbent is injected for a duration of several minutes. Desorbent flow is resumed, and the tracer and the aromatic isomers are eluted as in a liquid-solid chromatographic operation. The effluent can be analyzed by on-stream chromatographic equipment and traces of the envelopes of corresponding component peaks developed. Alternatively, effluent samples can be collected periodically and later analyzed separately by gas chromatography.

From information derived from the chromatographic traces, adsorbent performance can be rated in terms of capacity index for an extract component, selectivity for one isomer with respect to the other, and the rate of desorption of extract component by the desorbent. The capacity index may be characterized by the distance between the center of the peak envelope of the selectively adsorbed isomer and the peak envelope of the tracer component or some other known reference point. It is expressed in terms of the volume in cubic centimeters of desorbent pumped during this time interval. Selectivity, (B), for an extract component with respect to a raffinate component may be characterized by the ratio of the distance between the center of the extract component leak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

To further evaluate promising adsorbent systems and to translate this type of data into a practical separation process requires actual testing of the best system in a continuous countercurrent liquid-solid contacting device. The general operating principles of such a device have been previously described and are found in Broughton U.S. Pat. No. 2,985,589. A specific laboratory-size apparatus utilizing these principles is described in deRosset et al U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and raffinate and extract are being withdrawn through two more. All remaining access lines are inactive and when the position of the distributing valve is advanced by one index all active positions will be advanced by one bed. This simulates a condition in which the adsorbent physically moves in a direction countercurrent to the liquid flow. Additional details on the above-mentioned adsorbent testing apparatus and adsorbent evaluation techniques may be found in the paper "Separation of $C_8$ Aromatics by Adsorption" by A. J. deRosset, R. W. Neuzil, D. J. Korous, and D. H. Rosback presented at the American Chemical Society, Los Angeles, Calif., Mar. 28 through Apr. 2, 1971.

The feasibility of separating ethylbenzene from a feed mixture comprising ethylbenzene and a plurality of xylene isomers by selective adsorption of the xylene isomers, which was demonstrated by pulse test results, was confirmed by continuous testing in the laboratory-sized apparatus described above.

Adsorbents to be used in the process of this invention will comprise specific crystalline aluminosilicates or molecular sieves. Particular crystalline aluminosilicates encompassed by the present invention include crystalline aluminosilicate cage structures in which the alumina and silica tetrahedra are intimately connected in an open three dimensional network. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions. Thus, the crystalline aluminosilicates are often referred to as molecular sieves when the separation which they effect is dependent essentially upon distinction between molecules sizes as, for instance, when normal paraffins are separated from isoparaffins by using a particular crystalline aluminosilicate. In the process of this invention, however, the term molecular seives is not strictly suitable since the separation of specific $C_8$ aromatic isomers is dependent on electrochemical attraction of different isomer configurations rather than pure physical size differences in the isomer molecules.

In hydrated form, the crystalline aluminosilicates generally encompass those zeolites represented by the Formula 1 below:

Formula 1

$$M_{2/n}O:Al_2O_3:wSiO_2:yH_2O$$

where M is a cation which balances the electrovalence of the tetrahedra and is generally referred to as an exchangeable cationic site, $n$ represents the valence of the cation, $w$ represents the moles of $SiO_2$, and $y$ represents the moles of water. The cations may be any one of a number of cations which will be hereinafter described in detail.

The prior art has generally recognized that adsorbents comprising the type X structured and the type Y structured zeolites can be used in certain adsorptive separation processes. These zeolites are described and defined in U.S. Pat. Nos. 2,882,244 and 3,120,007 respectively. The terms "type X structured" and "type Y structured" zeolites as used herein shall include all zeolites which have general structures as represented in the above two cited patents.

The type X structured zeolite in the hydrated or partially hydrated form can be represented in terms of mole oxides as shown in Formula 2 below:

Formula 2

$$(0.9\pm0.2)M_{2/n}O:Al_2O_3:(2.5\pm0.5)SiO_2:yH_2O$$

where M represents at least one cation having a valence of not more than 3, $n$ represents the valence of M, and $y$ is a value up to about 9 depending upon the identity of M and the degree of hydration of the crystal. As noted from Formula 2 the $SiO_2/Al_2O_3$ mole ratio is 2.5±0.5. The cation M may be one or more of a number of cations such as the hydrogen cation, the alkali metal cation, or the alkaline earth cations, or other selected cations, and is generally referred to as an exchangeable cationic site. As the type X zeolite is initially prepared, the cation M is usually predominately sodium and the zeolite is therefore referred to as a sodium-type X zeolite. Depending upon the purity of the reactants used to make the zeolite, other cations mentioned above may be present, however, as impurities.

The type Y structured zeolite in the hydrated or partially hydrated form can be similarly represented in terms of mole oxides as in formula 3 below:

Formula 3

$(0.9\pm0.2)M_{2/n}O:Al_2O_3:wSiO_2:yH_2O$ where M is at least one cation having a valence not more than 3, $n$ represents the valence of M, $w$ is a value greater than about 3 up to 8, and $y$ is a value up to about 9 depending upon the identity of M, and the degree of hydration of the crystal. The $SiO_2/Al_2O_3$ mole ratio for type Y structured zeolites can thus be from about 3 to about 8. Like the type X structured zeolite, the cation M may be one or more of a variety of cations but, as the type Y zeolite is initially prepared, the cation M is usually predominately sodium. The type Y zeolite containing predmoninately sodium cations at the exchangeable cationic sites is therefore referred to as a sodium-type Y zeolite.

Cations occupying exchangeable cationic sites in the zeolite may be replaced with other cations by ion exchange methods generally known to those having ordinary skill in the field of crystalline aluminosilicates. Such methods are generally performed by contacting the zeolite with an aqueous solution of the soluble salt of the cation or cations desired to be placed upon the zeolite. After the desired degree of exchange takes place the sieves are removed from the aqueous solution, washed, and dried to a desired water content.

By such methods non-sodium cations which might be occupying exchangeable cationic sites as impurities in a predominately sodium-type X or sodium-type Y zeolite could be replaced with sodium cations by ion-exchanging the zeolite with a sodium hydroxide solution. The sodium cations themselves might be replaced or ion-exchanged with other specific cations to modify certain characteristics of the zeolite.

For the particular separation process of this invention where ethylbenzene is to be recovered as a raffinate component it is necessary that the zeolitic adsorbent possess selectivity for all of the xylene isomers with respect to ethylbenzene so that ethylbenzene will be rejected rather than adsorbed by the adsorbent. I have found that for the process of this invention crystalline aluminosilicate adsorbents comprising type Y zeolites having certain $SiO_2/Al_2O_3$ mole ratios and containing predominately sodium cations at the exchangeable cationic sites satisfies this selectivity requirement and the other adsorbent requirements previously discussed. More specifically, I have found this selectivity exists only for sodium-type Y zeolites having $SiO_2Al_2O_3$ mole ratios of greater than about 4.5. As the $SiO_2/Al_2O_3$ mole ratio of the sodium-form zeolites decreases from about 4.5 down to that of the type X zeolites ($2.5\pm0.5$), the selectivity of the zeolite for the xylene isomers with respect to ethylbenzene also decreases to the extent that adsorbents comprising such zeolites cannot be used in the process of this inventon. This result is unexpected since in many other separations performed with zeolitic adsorbents the silica to alumina ratio over the range covered by type X and type Y zeolites has generally not been found to be critical. Indeed, in many instances adsorbents comprising type X structured zeolites and adsorbents comprising type Y structured zeolites have been found to be generally equivalent. The result is additionally unexpected since it further confined to only certain zeolites with a broad type of zeolite; specifically it is confined to sodium-type Y zeolites having a $SiO_2/Al_2O_3$ mole ratio of greater than about 4.5.

The sodium-type Y zeolite can be produced by methods known to the art. The adsorbent for my process will typically comprise sodium-type Y zeolite in concentrations generally ranging from about 75 wt. % to about 98 wt. % of the adsorbent based on a volatile free composition. The remaining material in the adsorbent generally comprises amorphous silica or alumina or both which is present in intimate mixture with the zeolite material. This amorphous material may be an adjunct of the manufacturing process of the type Y zeolite (for example, intentionally incomplete purification of the zeolite during its manufacture) or it may be added to the relatively pure zeolite to aid in forming the zeolite into such particles as extrudates, aggregates, tablets, pills, or macrospheres. The adsorbent for my process will preferably be small particles in about 20 to 40 U.S. mesh particle size range which can be produced by grinding and screening the larger aforementioned particles.

In the process of this invention I have additionally found that the amount of water present on the zeolite adsorbent, as measured by loss on ignition (LOI) at a certain temperature, is important to the performance of the adsorbent. The amount of water present on the adsorbent is important because too much water decreases the adsorbent's ability to adsorb the xylene isomers and reject ethylbenzene and can additionally decrease the adsorbent's adsorptive capacity. Adsorbent water content is therefore an important process variable especially in continuous processes where the tendancy might be for the adsorbent to loose water with time. The water content of the zeolitic adsorbent can be determined by first weighing the adsorbent and thereafter contacting the adsorbent in a high temperature furnace at a temperature of from about 400° to about 900° C. under an inert purge gas stream such as nitrogen for a period of time sufficient to achieve a constant weight. The sample is then cooled under an inert atmosphere and weighed to determine the difference in weight between the adsorbent before it was passed into the oven and afterwards. The difference in weight is calculated as a loss on ignition and represents the water content of the adsorbent. The preferred water content of the adsorbent will be from about 0.2 to about 5 wt. % water measured by loss on ignition at 500° C. This amount of water may be maintained if necessary by adding water to the adsorbent either intermittently or more preferably continuously. The water may be added by itself or with the feed or desorbent material to maintain the desired concentration of water on the adsorbent.

EXAMPLE I

The following example is presented to illustrate the basis for the present invention and more specifically to illustrate the effect of silica to alumina ratio of zeolitic adsorbents on xylene selectivity with respect to ethylbenzene and is not intended to unduly limit the scope and spirit of the claims attached hereto.

This example presents results of five pulse tests which were performed on five individual adsorbents A, B, C, D, and E each in approximately 20–40 U.S. mesh particle size range and comprising respectively two sodium-type Y zeolites, two sodium-type X zeolites, and a calcium-type X zeolite. All adsorbents were calcined at 500° C. for 1 hour in a muffle furnace to achieve the same volatile content.

The testing apparatus was an adsorbent chamber containing approximately 70 cc of each adsorbent and was contained within a heat-control means in order to maintain essentially isothermal operations through the column. For each pulse test the column was maintained at a temperature of 150° C. and a pressure of 100 psig. to maintain liquid-phase operations. Gas chromatographic analysis equipment was attached to the column effluent stream in order to determine the composition of the effluent material at given time intervals. The feed mixture employed for each test contained 5 vol. % ethylbenzene, 5 vol. % para-xylene, 5 vol. % meta-xylene, 5 vol. % ortho-xylene, 5 vol. % n-nonane which was used as a tracer, and 75 vol. % desorbent material. The desorbent material employed was toluene.

The operations taking place for each test were as follows. The desorbent was run continuously at a nominal liquid hourly space velocity (LHSV) of 1.0 which amounted to about 1.17 cc per minute feed rate of desorbent. At some convenient time interval the desorbent was stopped and the feed mixture was run for a 10 minute interval at 1 LHSV. The desorbent stream was then resumed at 1 LHSV and continued to pass into the adsorbent column until all of the feed $C_8$ aromatics had been eluded from the column as determined by observing the chromatograph generated by the effluent material leaving the adsorption column. The sequence of operations usually takes about an hour. The 10 minute pulse of feed and subsequent desorption may be repeated in sequence as often as is desired.

From information derived from the chromatographic traces selectivities of the adsorbents for the xylene isomers with respect to ethylbenzene (P/E, M/E, and O/E) were calculated, by the method previously described, for each pulse test. The results for the five pulse tests are shown in Table 2 below.

Table 2

| Test | 1 | 2 | 3 | 4 | 5 |
|---|---|---|---|---|---|
| Adsorbent | A | B | C | D | E |
| Zeolite Type | Na-Y | Na-Y | Na-X | Na-X | Ca-X |
| $SiO_2/Al_2O_3$ by X-Ray | 4.9 | 3.7 | 3.0 | 2.4 | 2.4 |
| Selectivities: | | | | | |
| P/E | 2.28 | 1.50 | 1.05 | 1.20 | 2.18 |
| M/E | 4.10 | 2.08 | 1.10 | 1.20 | 4.09 |
| O/E | 2.23 | 1.95 | 1.39 | 1.11 | 3.21 |

Effect of $SiO_2/Al_2O_3$ Ratio of Na-X and Na-Y Zeolites on Xylene Selectivity

The test data shows that adsorbent A, comprising a sodium-type Y zeolite having a $SiO_2/Al_2O_3$ ratio of 4.9, produced the best xylene selectivities with respect to ethylbenzene of all the adsorbents tested. The selectivities are all above 2.0 indicating that the adsorbent will rather strongly adsorb all the xylene isomers and leave ethylbenzene to be recovered in high yields and high purity as a raffinate component. While adsorbent B, comprising a sodium-type Y zeolite having a $SiO_2/Al_2O_3$ ratio of 3.7, exhibits selectivities for all of the xylene isomer with respect to ethylbenzene only one of the three selectivities is greater than 2.0 which is considered necessary for the successful operation of the process of this invention. For adsorbents C and D, comprising sodium-type X zeolites having lower $SiO_2/Al_2O_3$ ratios than that of adsorbent B, the selectivities are all only slightly above 1.0 indicating essentially no selectivity for any of the xylene isomers with respect to ethylbenzene. Thus, these adsorbents are clearly not suitable in an adsorptive separation process to produce high yields of high-purity ethylbenzene. To obtain a selectivity distribution suitable for use in a process to produce ethylbenzene the sodium-type X zeolites must be calcium exchanged to produce a calcium-type X zeolite. This is shown by the results for test 5 performed with adsorbent E comprising a calcium-type X zeolite having the same $SiO_2/Al_2O_3$ ratio as that of adsorbent D. The selectivities shown for test 5 are now comparable to those obtained with adsorbent A which comprises sodium-type Y zeolites having a $SiO_2/Al_2O_3$ ratio of 4.9.

The data from tests 1 through 4 thus indicates that as the $SiO_2/Al_2O_3$ ratio decreases from 4.9 for adsorbent A to 2.4 for adsorbent D the selectivities of the adsorbents for all of the xylene isomers with respect to ethylbenzene also decreases. For successful use in the process of my invention the adsorbent must comprise a sodium-type Y zeolite having a $SiO_2/Al_2O_3$ mole ratio of greater than about 4.5.

I claim as my invention:

1. A process for separating ethylbenzene from a feed mixture comprising ethylbenzene and a plurality of xylene isomers which comprises contacting said mixture with an adsorbent consisting essentially of a sodium-type Y zeolite having a $SiO_2/Al_2O_3$ mole ratio of greater than about 4.5, selectively adsorbing substantially all of said xylene isomers to the substantial exclusion of the ethylbenzene, and thereafter recovering high-purity ethylbenzene.

2. The process of claim 1 further characterized in that said feed mixture contains para-xylene, meta-xylene, and ortho-xylene.

3. The process of claim 2 further characterized in that the concentration of ortho-xylene in said feed mixture is less than the concentration of either para-xylene or meta-xylene.

4. The process of claim 2 further characterized in that the concentration of para-xylene in said feed mixture is less than the concentrations of either ortho-xylene or meta-xylene.

5. The process of claim 2 further characterized in that the concentrations of ortho-xylene and para-xylene in said feed mixture are each less than the concentration of meta-xylene.

6. The process of claim 1 further characterized in that said feed mixture contains two xylene isomers.

7. The process of claim 1 including the step of treating the adsorbent containing said isomers with a desorbent material to remove the adsorbed xylenes therefrom as a fluid extract stream.

8. The process of claim 7 further characterized in that said desorbent material has an average boiling point substantially different from that of the feed mixture.

9. The process of claim 8 further characterized in that said desorbent material comprises toluene.

10. The process of claim 1 further characterized in being effected at a temperature within the range of from about 70° to about 450° F. and at a pressure within the range of from about atmospheric to about 500 psig.

11. The process of claim 10 further characterized in being effected in the liquid phase.

12. A process for separating ethylbenzene isomer from a hydrocarbon feed mixture consisting essentially of ethylbenzene and a plurality of xylene isomers which process comprises the steps of:
   a. contacting said mixture with an adsorbent comprising a sodium-type Y zeolite having a $SiO_2/Al_2O_3$ mole ratio of greater than about 4.5 at adsorption conditions to effect the selective adsorption of substantially all of said xylene isomers to the substantial exclusion of ethylbenzene;
   b. withdrawing from the adsorbent a raffinate stream comprising less selectively adsorbed ethylbenzene;
   c. contacting the adsorbent at desorption conditions with a desorbent material having a boiling point substantially different from that of the feed mixture to effect the removal of the selectively adsorbed xylene isomers; and,
   d. withdrawing from the adsorbent an extract stream comprising said isomers.

13. The process of claim 12 further characterized in that said feed mixture contains para-xylene, meta-xylene, and ortho-xylene.

14. The process of claim 13 further characterized in that the concentration of ortho-xylene in said feed mixture is less than the concentrations of either para-xylene or meta-xylene.

15. The process of claim 13 further characterized in that the concentration of para-xylene in said feed mixture is less than the concentrations of either ortho-xylene or meta-xylene.

16. The process of claim 13 further characterized in that the concentrations of ortho-xylene and para-xylene in said feed mixture are each less than the concentration of meta-xylene.

17. The process of claim 12 further characterized in that said feed mixture contains two xylene isomers.

18. The process of claim 12 further characterized in that said desorbent material comprises toluene.

19. The process of claim 12 further characterized in that said adsorption conditions and desorption conditions include a temperature within the range of from about 70° to about 450° F. and a pressure within the range of from about atmospheric to about 500 psig.

20. The process of claim 19 further characterized in being effected in the liquid phase.

* * * * *